United States Patent [19]

Takahara et al.

[11] Patent Number: 5,324,645
[45] Date of Patent: Jun. 28, 1994

[54] HIGHLY RETROVIRUS-PRODUCING DNA CONSTRUCT AND CELL LINE

[75] Inventors: Yoshiyuki Takahara; Kumiko Hamada, both of Kawasaki, Japan

[73] Assignee: Ajinomoto Co., Inc., Tokyo, Japan

[21] Appl. No.: 943,136

[22] Filed: Sep. 10, 1992

Related U.S. Application Data

[63] Continuation of Ser. No. 626,778, Dec. 13, 1990, abandoned.

[30] Foreign Application Priority Data

Dec. 14, 1989 [JP] Japan .................. 1-324317

[51] Int. Cl.⁵ .............. C12N 5/00; C12N 15/00; C12N 7/00; C12N 7/04
[52] U.S. Cl. ............... 435/172.1; 435/240.2; 435/172.2; 435/172.3; 435/320.1; 435/235.1; 435/236; 435/237
[58] Field of Search ............... 435/69.1, 91, 240.2, 435/172.3, 236, 320.1, 70.1, 70.4, 172.1, 172.2, 235, 237

[56] References Cited

U.S. PATENT DOCUMENTS 4,650,764 3/1987 Temin et al. .................. 435/240

OTHER PUBLICATIONS

Karasuyama et al. (1988) Eur. J. Immunol. 18 pp. 97–104.
Subramani et al. (1981) Molecular and Cellular Biology vol. 1 (9) pp. 854–864.

Primary Examiner—Robert J. Hill, Jr.
Assistant Examiner—Gian P. Wang
Attorney, Agent, or Firm—Oblon, Spivak, McClellland, Maier & Neustadt

[57] ABSTRACT

A highly retrovirus-producing DNA construct, which comprises a gene encoding retrovirus which is incorporated into a vector for gene amplification.

12 Claims, 2 Drawing Sheets

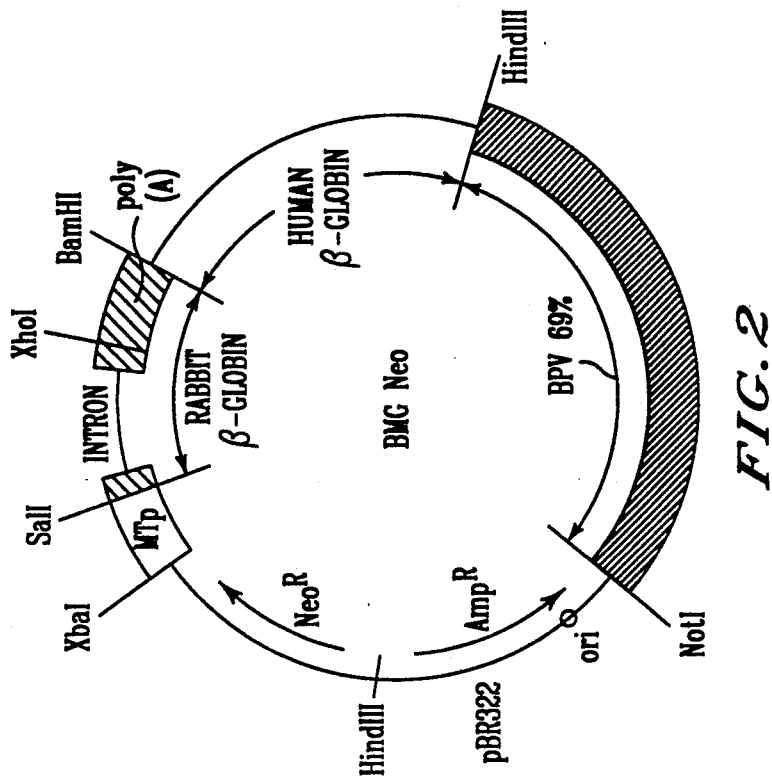
FIG. 2
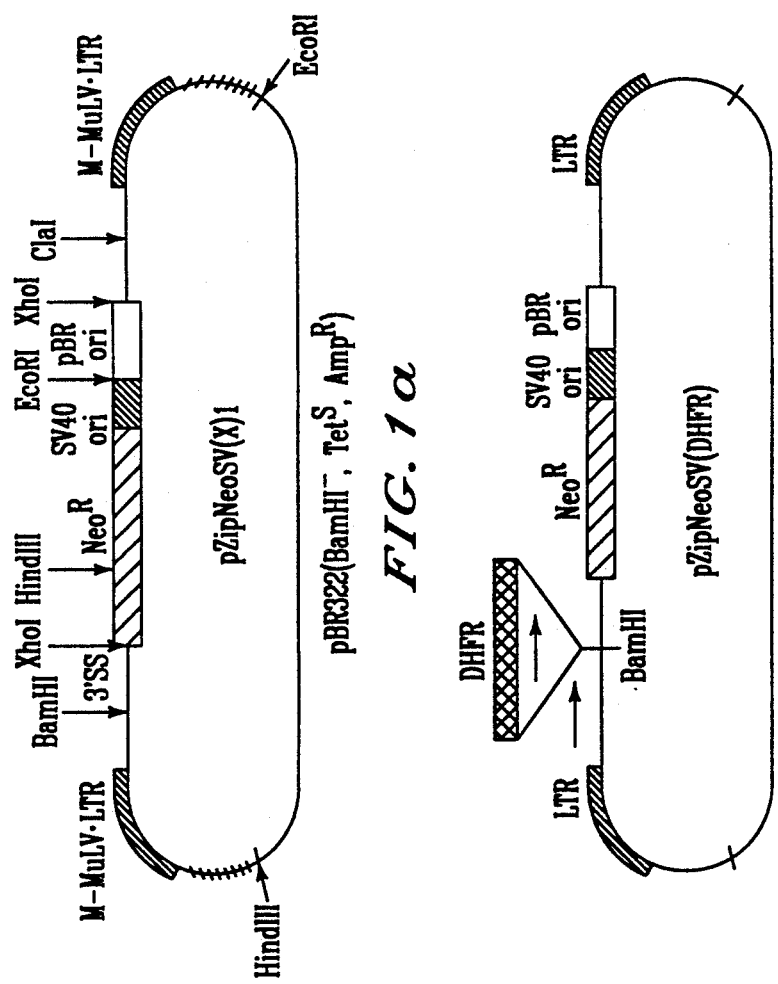
FIG. 1a
FIG. 1b

HIGHLY RETROVIRUS-PRODUCING DNA CONSTRUCT AND CELL LINE

This is a continuation of U.S. application Ser. No. 07/626,778, filed on Dec. 13, 1990, now abandoned.

BACKGROUND OF THE INVENTION

1. Field of the Invention

The present invention relates to a provirus DNA construct for producing retrovirus.

2. Description of the Background

The introduction of genes into cells is now used as an important research technique. For example, the function of a gene may be studied by introducing the same into cells. The gene may be introduced into primary culture cells or it may be introduced into reproductive cells to produce transgenic animals, mainly transgenic mice.

Alternatively, instead of studying the function of the gene, the function of a region encoding protein in the introduced gene may be studied. Also, the function of a gene region which regulates gene expression may also be studied.

In evaluating the progress of differentiation in a specific cell or the kinetics of a specified cell in vivo, a marker gene (for example, neomycin-resistant gene) is introduced into the specific cell to distinguish over other cells. This is also an important technique.

Next, it is likely that upon introducing a gene into productive cells to prepare a new transgenic animal, the transgenic animal may be utilized as livestock, an experimental animal or a pet animal.

Furthermore, it is also possible for humans to receive genetic treatment. Many genetic diseases caused by defects of a specific gene are known. It is also suspected that ordinary diseases such as cancer, autoimmune disease, diabetes, hypertension, infectious diseases, etc. are caused by deficiencies of a plurality of genes in combination. An attempt has thus been made to cure diseases by compensating for the defective gene or replacing the defective gene with a normal gene. At present, the introduction of a gene into productive cells of humans has been precluded due to moral considerations but attention has been focused, instead, on introducing genes into somatic cells for genetic treatment. The somatic cells to be so used are stem cells of the blood cell system, skin stem cells, hepatic stem cells, for example.

It is currently recognized that the most efficient method for introducing a gene into cells comprises using retrovirus. If circumstances require, a gene can be introduced into 100% of cells. In general, however, it is not easy to introduce a gene into primary culture cells or cells in vivo with a high efficiency as compared to the introduction into a cell line, even though retrovirus is used. In any case, it is important to contact a sufficient amount of retrovirus with cells, in order to enhance efficiency of gene introduction. Particularly in the case that the latter (primary culture cells or cells in vivo) is used, an amount of retrovirus greatly affects the efficiency.

When the cell line harbouring DNA for producing retrovirus particles is cultured, retrovirus can be obtained in the culture supernatant as virion. In such a state that retrovirus is suspended in medium, however, retrovirus is liable to be inactivated. Retrovirus is also liable to be inactivated by concentration operations. Accordingly, in order to efficiently perform gene introduction, it is necessary to obtain a medium having a high number of virion (which is referred to as titer and expressed by cfu/ml) having an activity of introducing a gene per unit volume. That is, virus-producing cells having a high titer are necessary.

Taking as an example gene introduction into blood cell stem cells used for genetic treatment using retrovirus, it is presumed that the stem cells into which a gene is to be introduced would be less than 0.1% of bone marrow cells, indicating that the density is very low. For this reason, a virus solution containing virion in an amount at least equivalent to, if possible, 10 times or 100 times $10^9$ to $10^{10}$ counts of bone marrow cells is generally required for bone marrow transplantation in a medium.

However, the upper limit of titer in the retrovirus-producing cell line for gene introduction obtained by introducing retrovirus vector pZipNeoSV(X)1 (C. L. Cepko et. al., Cell, 37, 1053, 1984) into helper cells $\phi 2$ (R. Mann et. al., Cell, 33, 153, 1983) ordinarily used is generally on the order of $10^4$ cfu/ml.

Provirus DNA encoding protein required for producing virion is incorporated into chromosomes of the retrovirus-producing cell line which is used for gene introduction, wherein components of virion are permanently produced by LTR (long terminal repeat) having the function of regulating DNA expression in the provirus. The components are produced from provirus DNA via mRNA; this mRNA per se is enveloped in these components to complete virion and virion is further released extracellularly. Natural virus infects other cells to release mRNA and enzymes in the virion. From this mRNA and enzymes, provirus DNA is formed and provirus DNA is further incorporated into chromosomes of the cells. By repeating this procedure, retrovirus proliferates.

However, retrovirus for gene introduction is defective in a part of the provirus DNA (packaging signal sequence, $\phi$). Therefore, the virus components produced from provirus DNA fail to envelope mRNA likewise produced from provirus.

On the other hand, when a DNA construct wherein DNA other than LTR and packaging signal of provirus is removed and instead, a DNA construct having inserted therein a gene to be introduced (gene construct so designed as to incorporate an optional gene, retrovirus vector) is introduced into helper cells, mRNA formed from this DNA is selectively enveloped in the virus components formed from provirus DNA to produce virion; this virion infects other cells and DNA is transcribed from the enveloped mRNA and this DNA is incorporated into chromosome. Since DNA capable of producing virus is not present in the incorporated DNA, there is no chance to reproduce virion. By such procedures, an optional gene can be introduced into cells, using retrovirus.

As described above, a method for gene introduction using retrovirus may be considered to be logically ideal but involves various problems for practical use. Firstly, an amount of retrovirus produced by helper cells should be increased, as described above. Secondly, while it occurs with a poor frequency, provirus DNA or mRNA formed thereby and retrovirus vector DNA or mRNA formed thereby are recombined with each other, whereby provirus might sometimes take up packaging signal therein to form natural virus capable of persistent infection. Where the two have high homology on their sequence, this phenomenon occurs (R. A.

Bosselman et. al., Mol. Cell. Biol., 7, 1797, 1987). Natural retrovirus has an ability of persistent infection so that there might be a danger of injuring the living body.

Thus, a need continues to exist for highly safe helper cells that do not allow natural virus to generate, and which overcome the above disadvantages.

SUMMARY OF THE INVENTION

Accordingly, it is an object of the present invention to provide helper cells in which provirus DNA having minimal homology with general retrovirus vector DNA has been introduced.

It is also an object of this invention to provide helper cells which ensure a virus titer as high as possible upon introduction of general retrovirus vector.

Further, it is an object of the present invention to provide a provirus DNA construct therefor.

These objects and others are provided by a highly retrovirus-producing DNA construct, containing a gene encoding retrovirus which is incorporated into a vector for gene amplification.

BRIEF DESCRIPTION OF THE DRAWINGS

FIGS. 1a–1b illustrate an outline of a retrovirus vector. FIG. 1a illustrates pZipNeoSV(X)1 and FIG. 1b illustrates pZipNeoSV(DHFR).

FIG. 2 illustrates an outline of an example of a vector for gene amplification.

DETAILED DESCRIPTION OF THE PREFERRED EMBODIMENTS

Figure 3:
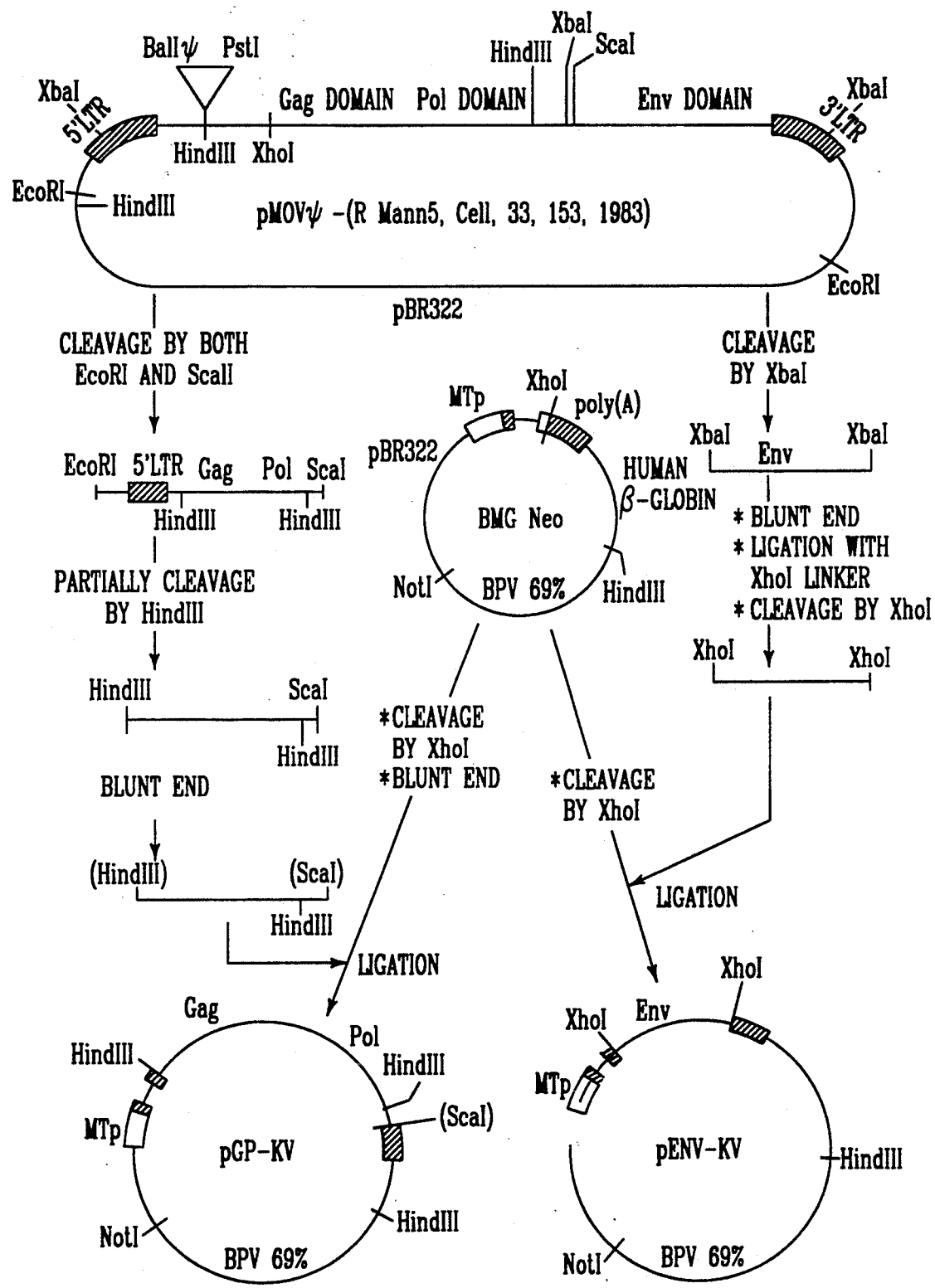
FIG. 3 illustrates an outline drawing showing DNA constructs pGP-KV and pENV-KV and the process used to prepare these constructs.

The present invention relates to a provirus DNA construct for production of retrovirus which may be used for introducing a gene into cells for purposes of studying the function of the gene, the production of genetic products by cells, the preparation of transgenic animals or genetic treatments for humans. The present invention also relates to helper cells having introduced therein this DNA construct, as well as a practical method for introducing retrovirus gene into helper cells.

FIG. 1 shows an outline of general retrovirus vector.

As shown in FIG. 1a, a ordinary retrovirus vector, LTR at the 5' end plays a role of promoter and enhancer for expressing the introduced gene (the gene is tentatively called X), a role in indicating splicing of mRNA, a further role in infecting cells with virus and then inserting viral DNA transcripted from viral mRNA into cell chromosomal DNA, etc. On the other hand, LTR at the 3' end participates in mRNA processing and stabilization by addition of poly A tail to viral mRNA and invasion of viral DNA into cell DNA. For expression of X, internal promoter may be used but promoter of LTR is not necessarily required; however, since a mechanism of invasion of viral DNA into cell DNA has not yet been sufficiently clarified, LTR is mandatorily required for retrovirus vector at present.

Therefore, in order to minimize homology of provirus DNA with vector DNA, it is necessary to remove LTR of provirus and substitute this function with another DNA unit. Also in provirus, LTR plays roles in expressing gag, pol and env genes (provirus gene is roughly classified into and called gag domain, pol domain and env domain, in view of their roles), and splicing and stabilizing mRNA. In gag and pol genes, translation of protein is initiated from mRNA starting with initiation codon of gag, but in env gene, protein is translated from the spliced mRNA coding for env gene. For this reason, in the present invention, gag and pol genes and env gene are incorporated into separate vectors for gene expression. By incorporating gag and pol genes separately from env gene, it may be expected to attain the effect of further reducing frequency of occurrence of natural virus due to recombination of virus vector gene and provirus gene.

As a vector for expression of gag, pol and env genes, for example, a vector shown in FIG. 2 is conceivable. In this example, metallothionein promoter (MTp) is used as promoter and poly A tail of $\beta$-globin is used as poly A tail for stabilization of mRNA but the promoter and poly A tail are not limited thereto. Any promoter and poly A tail may be used so long as they have low homology to LTR of retrovirus vector. For example, promoter of SV40, promoter of cytomegalovirus, poly A tail of SV40, poly A tail of metallothionein, for example, may also be used.

Next, in order to achieve a high titer, it is possible to produce the products of gag, pol and env genes in helper cells in large quantities. This can be attained by increasing the number of copies of gag, pol and env DNAs in helper cells.

FIG. 3 shows an example of the DNA construct for increasing the number of DNA copies and a method for construction. That is, gag, pol or env DNA is inserted into circular DNA containing provirus DNA of bovine papilloma virus (BPV). This DNA construct increases the number of copies in cells, while maintaining the form of circular DNA to reach 100 copies at maximum. Even after cell division, this copy number is stably maintained.

For example, a DNA construct where the minimum unit of gag and pol genes of retrovirus, namely, provirus DNA from initiation codon of gag to termination codon of pol, is inserted into vector as shown in FIG. 2 is termed pGP-KV and a DNA construct where provirus DNA from initiation codon of env to termination codon of env is inserted into the vector is termed pENV-KV.

pGP-KV and pENV-KV are simultaneously transfected to the cell line, e.g., NIH3T3 or C127, in which BPV is considered to stably maintain a high copy number. The transfectant is selectively proliferated by neomycin (G418) to obtain the transfectant as clones. Clones which can maintain a high copy number are selected from these clones and the clones are helper cells.

In obtaining helper cells, pGP-KV may be transfected to cells, clones having a high copy number of gag and pol genes are then selected, pENV-KV may be transfected to the clones, and clones having high copy number in any of gag, pol and env genes may be selected. Conversely, pENV-KV may be firstly transfected and pGP-KV may then be transfected. For selection of the transfectant, G418 is used in the case of using the vector shown in FIG. 2, since neomycin-resistant gene is used. In the case that hygromycin-resistant gene is used as vector, hygromycin may be used. Any other selection system may also be used.

The provirus incorporated into helper cells according to the present invention does not contain the LTR portion and has low homology to retrovirus vector. Therefore, the provirus is characterized by minimized probability of generating virus capable of persistent infection.

By incorporating, for example, retrovirus vector N2 (G. Keller et. al., Nature, 318, 149, 1985), for example, having much portion of gag-sequence overlapping provirus DNA reported to generate infectious virus by recombination, irrespective of a high titer (R. A. Bosselman et. al., Mol. Cell. Biol., 7, 1797, 1987), a virus solution can be obtained having a virus titer of more than $10^5$ to $10^7$ cfu/ml and capable of persistent infection.

As the env gene used in pENV-KV, different genes may be used depending upon the intended purpose. If the gene is introduced into mouse cells alone, env gene of Moloney mouse leukemia virus, e.g., pMOV$\phi^-$ (R. Mann et. al., Cell, 33, 153, 1983) or the like is used. In the case that animal species other than a mouse, e.g., animal species including humans are used over a wide range, a mutant of mouse leukemia virus, e.g., Amphotrophic Virus 4070A env gene (R. D. Cone, Proc. Natl. Acad. Sci. USA, 81, 6349, 1984) or the like may be used. For example, DNA from Sph I site to Cla I site of Amphotrophic Virus 4070A provirus DNA may be substituted with DNA from Sph I site to Cla I site in Moloney mouse leukemia virus provirus DNA.

The drawings will now be described in more detail.

FIG. 1a–1b show an outline of ordinary retrovirus vector. FIG. 1a shows pZipNeoSV(X)1 (C. L. Cepko et. al., Cell, 37, 1053, 1984) and FIG. 1b shows pZipNeoSV (DHFR) obtained by excising pSV2-dhfr (s. Subramani et. al., Mol & Cell. Biol., 1, 854, 1981), converting the end into the blunt end with Klenow DNA polymerase and inserting into the Bam HI site of pZipNeoSV(X)1 using Bam HI linker, wherein DHFR is mouse dihydrofolate reductase cDNA.

FIG. 2 shows an outline of an example of vector for gene amplification (H. Karasuyama et. al., Eur. J. Immunol., 18, 97, 1988).

FIG. 3 is an outlined drawing showing novel DNA constructs pGP-KV and pENV-KV and the procedure of constructing these constructs.

The present invention will now be illustrated by reference to certain examples which are provided solely for purposes of illustration and are not intended to be limitative.

EXAMPLE 1 (CF. FIG. 3)

After pMOV$\phi^-$ (R. Mann et. al., Cell, 33. 153, 1983) was cleaved with Eco RI and Sca I, DNA fragment containing gag and pol was excised and further partially cleaved with Hind III to give Hind III-Sca I fragment. The fragment was blunt-ended using Klenow fragment DNA polymerase I. On the other hand, vector BMGNeo containing metallothionein promoter, BPV, etc. (FIG. 2, H. Karasuyama et. al., Eur. J. Immunol., 18, 97, 1988) was cleaved with Xho I and blunt-ended with Klenow fragment DNA polymerase I. Both fragments which had been blunt-ended were ligated with each other to give pGP-KV.

On the other hand, pMOV$\phi^-$ was cleaved with Xba I to give about 2.3 kb of DNA fragment containing env. The fragment was made blunt end with Klenow fragment DNA polymerase I followed by ligation with Xho I linker. The ligated product was treated with Xho I to prepare Xho I site, which was ligated with BMGNeo vector cleaved with Xho I. Thus, pENV-KV was obtained.

EXAMPLE 2

NIH3T3 cell line was cultured in DMEM (Dulbecco's Modified Eagle Medium) charged in a Petri dish of 10 cm diameter. At the time when cells grew to $1 \times 10^6$, pGP-KV and pENV-KV were simultaneously transfected to the cells according to the method of C. Chen et. al. (C. Chen et. al., Mol. Cell. Biol., 7, 2745, 1987), wherein 5 µg of DNA was used per $1 \times 10^6$ cells.

On the day succeeding the transfection, the medium was exchanged. Further 2 days after, the cells were inoculated in DMEM supplemented with 250 µg/ml of G418 in a cell density of $1 \times 10^4$ to $1 \times 10^5$/10 cm Petri dish. Every 3 to 4 other days, the medium was replaced with DMEM supplemented with 250 µg/ml of G418. About 2 weeks after, the grown colonies were fished in a 24 well plate by the cup method and subcultured in DMEM supplemented with 250 µg/ml of G418.

At the time when the cells were proliferated to 80 to 90% of the bottom area, the culture supernatant was collected and the activity of reverse transcriptase (pol product) in the culture supernatant was determined according to the method of S. Goff et. al. (J. Virol., 38, 239, 1981).

A part of the clones having a high reverse transcriptase activity was lyophilized and stored. At the same time, the remaining clones were proliferated to 0.5 to $1 \times 10^7$ counts and episomal DNA was prepared by the method of Hirt (J. Mol. Biol., 26, 365, 1967). With respect to a DNA sample capable of hybridizing with env probe (Sca I site→Cla I site, about 1.8 kb) by dot blotting hybridization, southern blotting pattern of the selected clone was examined in more detail.

That is, the DNA sample was cleaved with Hind III followed by electrophoresis on 0.7% agarose gel. After the gel was denatured with an alkali, it was blotted on a nitrocellulose filter. The filter was hybridized with gag-pol probe (Xho I site→Nde I site, about 3.8 kb) or env probe. With any of gag-pol probe and env probe, clones showing strong bands at the positions presumed to be gag, pol and env, respectively were selected.

These clones were further recloned. That is, the cloned cells were inoculated on a 96 well plate in a ratio of 0.3 cells/well. After culturing for 2 weeks (DMEM supplemented with 250 µg/ml of G418), the activity of reverse transcriptase in the supernatant of the wells in which clones were formed was determined and clones having a high activity were selected.

The selected clones were proliferated to $1 \times 10^7$ respectively. According to the method of C. Chen et. al., 5 µg of retrovirus vector DNA containing neomycin-resistant gene and DHFR (dihydrofolate reductase) shown in FIG. 1b and 0.5 µg of pSV2Gpt DNA as a transfection marker (R. C. Mulligan et. al., Proc. Natl. Acad. Sci. USA, 78. 2072, 1981) were simultaneously transfected.

On the next day, the medium was exchanged with DMEM. Further 2 days after, the cells were inoculated in selective medium (DMEM containing 15 µg/ml of hypoxanthine, 2 µg/ml of aminopterin, 5 µg/ml of thymidine, 5 µg/ml of glycine, 25 µg/ml of mycophenolic acid, 250 µg/ml of xanthine and 150 µg/ml of L-glutamine) supplemented with 250 µg/ml of G418 in a cell density of $1 \times 10^4$ to $1 \times 10^5$/10 cm Petri dish. Incubation was performed for 2 weeks, while replacing the medium with selective medium every 3 to 4 other days. The formed clones were isolated and transferred to a 24 well plate. A virus titer in the culture supernatant at the time when the cells were proliferated to 80 to 90% of the bottom area was determined.

The clones showing a high titer (referred to as primary clones) were further recloned. That is, the cloned cells were inoculated on a 96 well plate in a ratio of 0.3 cells/well. After culturing in selective medium supplemented with 250 μg/ml of G418 for 2 weeks, the formed clones (referred to as secondary clones) were transferred to a 24 well plate. A virus titer in the culture supernatant at the time when the cells were proliferated to 80 to 90% of the bottom area was determined.

The titer was determined as shown in DNA Cloning, Vol. III (Ed. by D. M. Glover, IRL Press, page 203, 1987). However, the medium was replaced with DMEM supplemented with 250 μg/ml of G418, 2 days after the viral infection and the medium was exchanged with the DMEM every 3 to 4 other days and, colonies were counted about 2 weeks after to calculate cfu/ml.

Titers of the primary clones and the secondary clones are shown in Tables 1 and 2, respectively.

As helper cells for purpose of comparison, retrovirus vector shown in FIG. 1b was transfected to φ2 strain. After culturing in DMEM supplemented with 250 μg/ml of G418 for 2 weeks, primary clones were obtained. The clones were further recloned to give secondary clones. Titers of the primary clones and the secondary clones are shown in Tables 1 and 2, respectively.

TABLE 1

| Helper Cell Line | Number of Clone Measured | Titer of Primary Clone Number* of Primary Clones Classified by Titer (cfu × $10^{-4}$/ml) | | | | | | |
|---|---|---|---|---|---|---|---|---|
| | | 5 | 4 | 3 | 2 | 1 | 0.1 | <0.1 |
| A-77 | 5 | 0 | 0 | 1 | 1 | 0 | 0 | 3 |
| A-82 | 30 | 0 | 0 | 3 | 0 | 0 | 3 | 24 |
| A-57 | 22 | 1 | 1 | 0 | 0 | 2 | 3 | 15 |
| A-70 | 21 | 0 | 0 | 1 | 0 | 3 | 0 | 17 |
| A-54 | 23 | 0 | 0 | 0 | 0 | 0 | 2 | 21 |
| A-89 | 24 | 0 | 0 | 0 | 0 | 4 | 3 | 17 |
| A-85 | 19 | 0 | 0 | 0 | 0 | 1 | 1 | 17 |
| A-79 | 21 | 0 | 0 | 0 | 0 | 1 | 0 | 20 |
| B-18 | 38 | 0 | 0 | 0 | 0 | 1 | 5 | 32 |
| φ2 | 19 | 0 | 0 | 0 | 4 | 14 | 1 | 0 |

*The culture supernatant of the primary clones was measured and the number of clones was designated with respective classes of titer.

TABLE 2

| Helper Cell Line | Number of Primary Clone | Number of Secondary Clone Measured | Titer of Secondary Clone Number** of Secondary Clones Classified by Titer (cfu × $10^{-4}$/ml) | | | | | | |
|---|---|---|---|---|---|---|---|---|---|
| | | | 20 | 10 | 8 | 6 | 4 | 2 | 1 | <1 |
| A-77 | #141 | 4 | 0 | 0 | 0 | 1 | 0 | 0 | 0 | 3 |
| A-82 | #127 | 2 | 0 | 0 | 1 | 0 | 0 | 0 | 0 | 1 |
| | #128 | 23 | 0 | 0 | 1 | 0 | 1 | 0 | 0 | 21 |
| A-57 | #57 | 16 | 1 | 2 | 0 | 1 | 0 | 1 | 0 | 11 |
| | #61 | 91 | 10 | 16 | 3 | 4 | 3 | 3 | 4 | 48 |
| A-70 | #160 | 17 | 0 | 2 | 1 | 0 | 1 | 2 | 1 | 10 |
| φ2 | #7 | 20 | 0 | 0 | 0 | 0 | 1 | 3 | 2 | 14 |
| | #24 | 24 | 0 | 0 | 0 | 0 | 0 | 3 | 2 | 19 |

**The culture supernatant of the secondary clones was measured and the number of clones was designated with respective classes of titer.

As is clear from Tables 1 and 2 above, virus-producing cells having a titer of about 10 times could be produced by using helper cells prepared from pGP-KV and pENV-KV, as compared to the case of using φ2 helper cells.

EXAMPLE 3

Helper cells A-57, A-70, A-77, A-82 and φ2 were cultured in DMEM. The whole DNAs were extracted from $5 \times 10^6$ of cells at the exponential growth phase according to the method of T. Maniatis (Molecular Cloning, Cold Spring Harbor Lab., page 280, 1982).

After 1.5 μg of DNAs were cleaved with Hind III, the cleavage product was subjected to 0.7% agarose gel electrophoresis for Southern blotting on a nitrocellulose filter. The filter was subjected to hybridization using $^{32}$P-labeled gag-pol probe (same as in Example 2) or $^{32}$P-labeled env probe (same as in Example 2). Hybridization was likewise performed using $^{32}$P-labeled actin probe (chicken actin, Nco I site→Taq I site, 770 bp, Clevel et. al., Cell, 20, 95, 1980), according to the general method of T. Maniatis (same as above). Assuming that one copy of actin DNA would be present in one cell, the number of gag, pol or env DNA copies was calculated. The results are shown in Table 3. As is noted, φ2 had one copy of gag, pol or env DNA per one cell, whereas A-77, A-82, A-57 and A-70 had 100 to 500 copies of gag, pol or env DNA.

TABLE 3

| Helper Cell Line | Number of Copies of gag, pol or env DNA in helper Cell Line Number of Copy/Cell | |
|---|---|---|
| | Gag, pol DNA | env DNA |
| A-77 | ca. 100 | ca. 100 |
| A-82 | ca. 500 | ca. 500 |
| A-57 | ca. 100 | ca. 100 |
| A-70 | ca. 200 | ca. 300 |
| φ2 | 1 | 1 |

Having described the present invention, it will be apparent to one of ordinary skill in the art that many changes and modification can be made to the above embodiments without departing from the spirit and scope of the present invention.

What is claimed as new and desired to be secured by Letters Patent of the U.S. is:

1. A retrovirus-producing DNA construct, comprising:
    a gene encoding said retrovirus and a vector for gene amplification, wherein said gene encoding said retrovirus does not contain a retrovirus long terminal repeat sequence.

2. The DNA construct of claim 1, wherein said retrovirus encoding gene contains provirus DNA from the initiation codon of the gag domain to the termination codon of the pol domain of said retrovirus.

3. The DNA construct of claim 1, wherein said retrovirus encoding gene contains provirus DNA from the initiation codon of the env domain to the termination codon of the env domain of said retrovirus.

4. The DNA construct of claim 1, comprising a metallothionein promoter.

5. The DNA construct of claim 1, wherein said vector for gene amplification is BMGNeo.

6. The DNA construct of claim 5, wherein said construct is pGP-KV.

7. The DNA construct of claim 5, wherein said construct is pENV-KV.

8. A retrovirus producing helper cell line containing a DNA construct comprising a gene encoding said retrovirus and a vector for gene amplification, wherein said gene encoding said retrovirus does not contain a retrovirus long terminal repeat sequence.

9. The cell line of claim 8, further comprising a retrovirus vector DNA construct.

10. The cell line of claim 9, wherein said retrovirus vector DNA construct is pZipNeoSv (DHFR) or N2.

11. The cell line of claim 10, wherein said retrovirus vector DNA construct is pZipNeoSv (DNFR).

12. The cell line of claim 8, said cell line containing up to 100 copies of said DNA construct as circular DNA.

* * * * *

UNITED STATES PATENT AND TRADEMARK OFFICE
CERTIFICATE OF CORRECTION

PATENT NO. : 5,324,645
DATED : June 28, 1994
INVENTOR(S) : Yoshiyuki Takahara, et al It is certified that error appears in the above-indentified patent and that said Letters Patent is hereby corrected as shown below:

Column 5, Line 45, "33. 153," should read --$\underline{33}$, 153,--

Column 6, Line 9, "1 X 104" should read --1 X $10^4$--

Column 6, Line 45, "1 X 107" should read --1 X $10^7$--

Column 6, Line 51, "78. 2072," should read --$\underline{78}$, 2072,--

Signed and Sealed this

Eleventh Day of July, 1995

Attest:

BRUCE LEHMAN

Attesting Officer

Commissioner of Patents and Trademarks